US006621569B2

United States Patent
Sones

(10) Patent No.: US 6,621,569 B2
(45) Date of Patent: Sep. 16, 2003

(54) ILLUMINATOR FOR MACHINE VISION

(75) Inventor: Richard A. Sones, Cleveland, OH (US)

(73) Assignee: Applied Vision Company LLC, Akron, OH (US)

(*) Notice: Subject to any disclaimer, the term of this patent is extended or adjusted under 35 U.S.C. 154(b) by 0 days.

(21) Appl. No.: 09/865,135

(22) Filed: May 24, 2001

(65) Prior Publication Data

US 2001/0048524 A1 Dec. 6, 2001

Related U.S. Application Data

(60) Provisional application No. 60/207,689, filed on May 26, 2000.

(51) Int. Cl.$^7$ ............................................... G01N 21/00
(52) U.S. Cl. ................................. 356/237.2; 356/240.1
(58) Field of Search ........................... 256/239.4, 239.5, 256/239.6, 240.1, 237.1, 239.3, 237.2; 250/223 B

(56) References Cited

U.S. PATENT DOCUMENTS

| | | | | |
|---|---|---|---|---|
| 3,782,836 A | * | 1/1974 | Fey et al. ................... | 356/209 |
| 3,980,890 A | * | 9/1976 | Heckrodt et al. ............ | 250/560 |
| 4,161,366 A | * | 7/1979 | Bol et al. .................... | 356/56 |
| 4,173,278 A | * | 11/1979 | Reitter ........................ | 198/461.1 |
| 4,606,635 A | | 8/1986 | Miyazawa et al. ........ | 356/240.1 |
| 4,614,427 A | * | 9/1986 | Koizumi et al. ............ | 356/237 |
| 4,758,084 A | | 7/1988 | Tokumi et al. ............. | 356/239.4 |
| 6,025,909 A | * | 2/2000 | Juvinall et al. ............ | 356/239.4 |

OTHER PUBLICATIONS

Bob Kirzl, Chiu Technical Corp., "Points of light", Design News, Cahners Publishing Company, (Feb. 7, 1994).
Carl H. Vandommelen, "Choose the Right Lighting for Inspection", Test & Measurement World, p. 53–54, 56–57, (Oct. 1996).

* cited by examiner

Primary Examiner—Jordan M. Schwartz
(74) Attorney, Agent, or Firm—Robert J. Clark; Hahn Loeser & Parks, LLP

(57) ABSTRACT

The present invention is directed to inspection of sealing surfaces of containers for defects which may prevent proper sealing of the container. The present invention provides an inspection apparatus, system, and method for dark-field machine vision inspection of containers, such as glass containers or other containers having a sealing surface. The illumination system provides a dual directional helical illumination technique, which enhances the ability to distinguish any defects in the sealing surface area. The illumination system may also provide the ability to adjust the diameter of a circular illumination pattern, so as to allow adjustability and optimization of the illumination characteristics for differing container configurations.

18 Claims, 4 Drawing Sheets

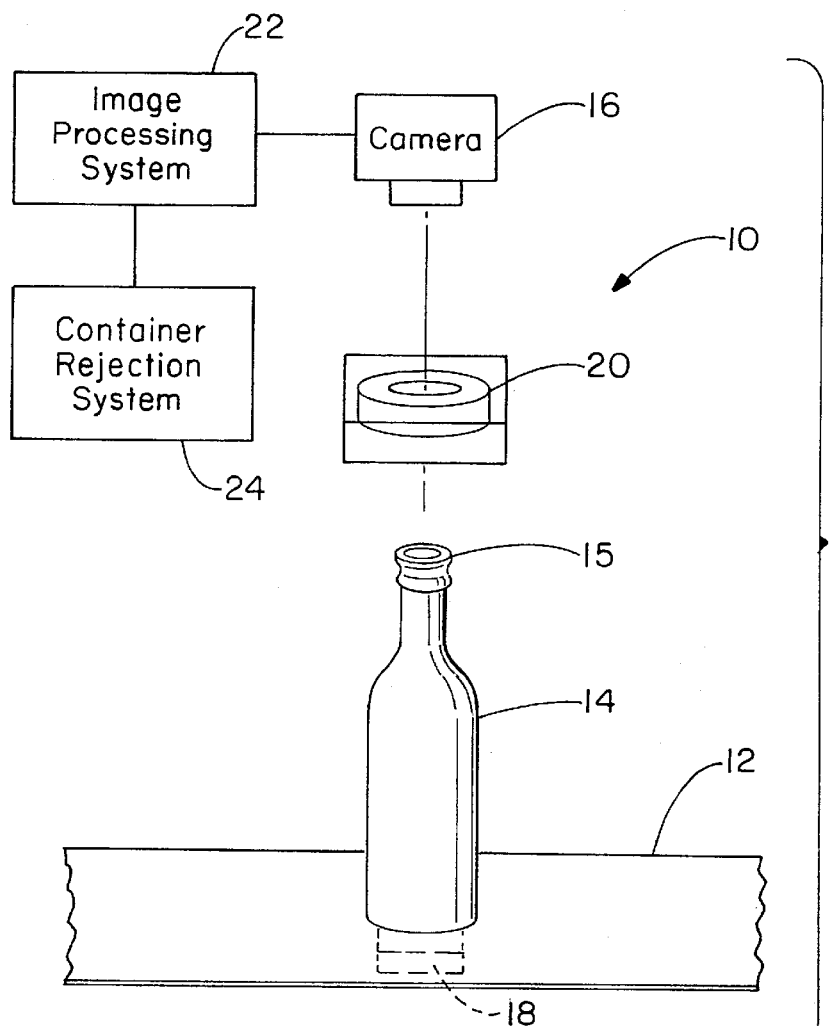
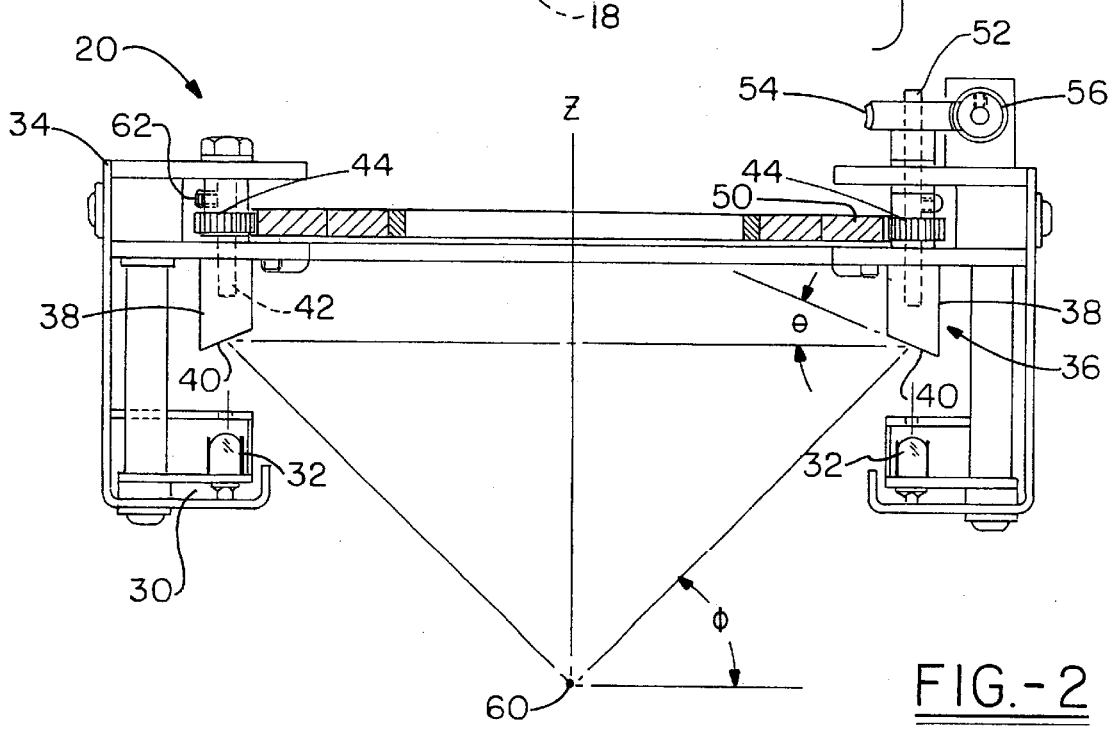

ILLUMINATOR FOR MACHINE VISION

This application claims the benefit of U.S. Provisional Application No. 60/207,689. filed May 26, 2000. The present invention is directed to inspection of containers, and more particularly to a method and apparatus for detecting defects at the sealing surface area of a container, and illumination systems and methods.

BACKGROUND OF THE INVENTION

An ideal glass container has a smooth and flat sealing surface against which the container closure makes a tight seal. Sealing-surface defects such as cracks, scratches, roughness, chips, and other disconformities in the surface may lead to improper seating of the closure, and can prevent hermetic sealing of the container. This in turn leads to spoilage of the container contents. Accordingly, it is necessary to detect such defects on the mouths of these bottles to prevent use of bottles with defects.

Machine vision technology is widely used to inspect the sealing surfaces of glass containers as they are being manufactured or for reuse, to automatically reject defective containers. The inspection of the sealing surface by means of machine vision requires suitable illumination of the sealing surface, and the characteristics of the illumination should allow confident inspection without generating spurious reflections from other portions of the container or its surroundings. Different containers require different illumination techniques for optimum visibility of defects. Two well-known illumination strategies used in sealing-surface inspection are "light-field" and "dark-field" illumination. With light-field illumination, the entire sealing surface is visible in the image, and defects appear as light or dark structures on this surface. With dark-field illumination, the sealing surface is not visible, or is barely visible, in the image, but defects appear as bright structures.

Although various methods of detecting defects on a bottle mouth have been proposed, such methods have not provided optimum illumination of the sealing surface. As the defects which may be present and the character of the defects can vary greatly, the illumination of the surface should facilitate identification of any such defects, and yet prior systems have not adequately provided this ability. To detect the widely differing types of defects, it would be desirable to provide illumination which is directed at the surface from differing angles to facilitate defect identification. Further, no such methods are adaptable to different container configurations in a simple and effective manner. It would also be desirable to provide an illumination system and characteristics which allow adaptability to different container configurations and sealing surface characteristics. Other prior art inspection methods and systems have required a container to be rotated 360 degrees under one or more light beams to fully illuminate the sealing surface, but such physical manipulation causes difficulties, as the system is more mechanically complex, and requires an extended dwell time for inspection, which adversely impacts on production in the manufacturing process. It would therefore also be desirable to provide a system and method which allows for inspection without physical manipulation of the container, and at very high production speeds.

SUMMARY OF THE INVENTION

The present invention provides an inspection system and methods, and illumination system and methods for dark-field machine vision inspection of containers, such as glass containers or other containers having a sealing surface. The illumination system provides a dual directional helical illumination technique, which enhances the ability to distinguish any defects in the sealing surface area. The illumination system may also provide the ability to adjust the diameter of a circular illumination pattern, so as to allow adjustability and optimization of the illumination characteristics for differing container configurations. For example, containers such as wide-mouth glass containers present difficulties in properly illuminating the surface, and the present invention allows illumination characteristics to be modified to account for such unique containers. For containers having a sealing surface of about 35 mm or larger, it has been difficult to properly illuminate the entire surface for inspection, which the present invention resolves. The use of a helical illumination pattern has also been found to enhance defect visibility in some circumstances, compared to other light-field or dark-field illumination patterns. The simultaneous use of both clockwise and counter-clockwise illumination patterns also improves defect detection. The ability to adjust the diameter of the helical light field allows the illumination to be optimized for any given type of container, and allows rapid changeover from one type of container to another.

In one embodiment of the present invention, these and other advantages are provided by a dark field illuminator comprising a means for projecting a first plurality of collimated light beams in a clockwise helical illumination pattern onto a sealing surface of a container, means for projecting a second plurality of collimated light beams in a counter-clockwise helical illumination pattern onto the sealing surface of the container, and means for recording an image of the illuminated sealing surface. The clockwise and counter-clockwise helical illumination patterns are projected simultaneously onto the sealing surface of the container at a predetermined angle such that the light beams are reflected away from the means for recording an image of the illuminated sealing surface unless a defect is encountered such that at least a portion of the light beam is reflected toward the means for recording an image of the illuminated sealing surface.

In another embodiment of the present invention, these and other advantages are provided by a dark field illuminator comprising a first set of a plurality of mirrored surfaces, a second set of a plurality of mirrored surfaces, and a plurality of light sources each positioned to direct a beam of light toward one of the first set and the second set of the plurality of mirrored surfaces. The mirrored surfaces of the first set of the plurality of mirrored surfaces are positioned to reflect the beams of light at a predetermined angle in a clockwise helical illumination pattern and the mirrored surfaces of the second set of the plurality of mirrored surfaces are positioned to reflect the beams of light at a predetermined angle in a counter-clockwise helical illumination pattern.

In another embodiment of the present invention, these and other advantages are provided by a method for inspecting a sealing surface of a container comprising the steps of a) providing a container having a sealing surface, b) illuminating the sealing surface with a clockwise helical illumination pattern and a counter-clockwise helical illumination pattern at a predetermined angle from an illuminator device, c) recording an image of the illuminated sealing surface, and d) determining whether a defect exists on the sealing surface.

In still another embodiment, these and other advantages are provided by a machine vision system for inspecting a sealing surface of containers comprising an illuminator comprising a plurality of mirrored surfaces which redirect collimated light beams at a predetermined angle in a clockwise and counter-clockwise helical pattern onto the sealing surface of the container, a camera positioned to record an image of the sealing surface when the surface is illuminated by the illuminator, a container positioning sensor which determines when a container sealing surface is properly positioned with respect to the camera and the illuminator, an image inspection system for evaluating whether the image shows a defect on the sealing surface, and a container rejection system which selectively segregates the containers based on whether any defects are detected on the sealing surface. The illuminator directs the light beams onto the sealing surface such that the light beams will be directed away from the camera unless a defect in the sealing surface is encountered wherein at least a portion of the beam will be redirected toward the camera.

BRIEF DESCRIPTION OF THE DRAWINGS

A better understanding of the present invention will be had when reference is made to the accompanying drawings, wherein:

FIG. 1 is a schematic illustration of a machine vision system and container inspection system according to the invention;

FIG. 2 is a side elevational view of the illumination system according to an embodiment of the invention;

DETAILED DESCRIPTION OF THE DRAWINGS

Figure 3:
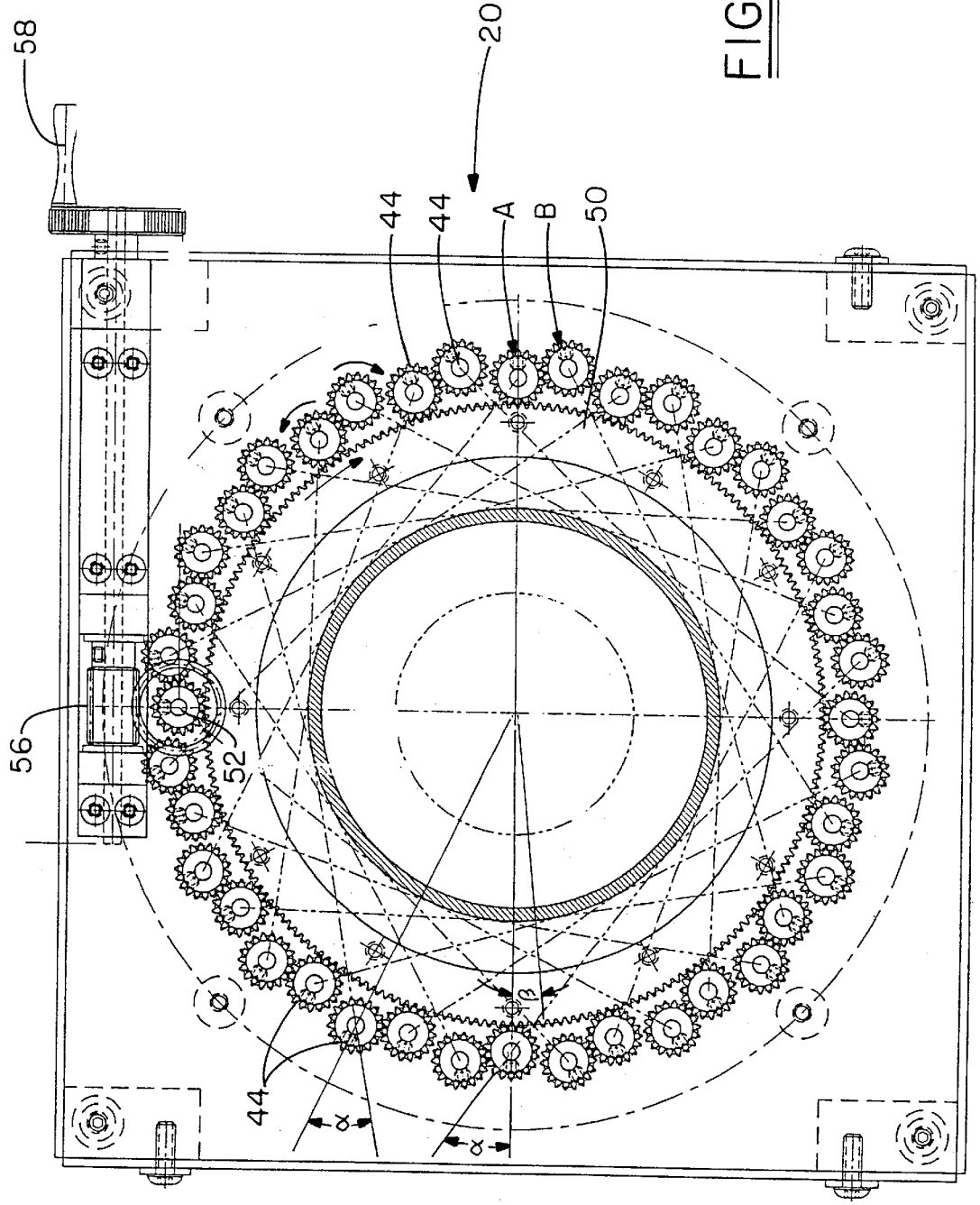
FIG. 3 is a top view of the assembly as shown in FIG. 2.

Referring to FIG. 1, the machine vision system 10, according to an embodiment of the invention may include an illumination system or apparatus 20, mounted above a conveyor 12 carrying glass containers 14. For inspection of the sealing surface of container 14, the illumination system 20 is mounted above and in alignment so the centers of the containers pass directly underneath the center of the illuminator 20. A camera 16 is mounted above the illuminator 20, and provides an image forming system to generate an image of the sealing surface 15. As containers 14 are moved past the machine vision system 10, a photoelectric part-present sensor 18 or other suitable mechanism is typically used to trigger operation of the illumination system 20 in a strobed fashion, and an image is acquired of the sealing surface 15. An image processing system 22 may be used to analyze the image and determine if defects exist in the sealing surface 15, and if so, a container reject system 24 may be used to remove the defective container from the conveyor 12. The machine vision system 10 may also be used to inspect objects other than containers 14, or may be used in other ways other than for inspection.

Referring now to FIGS. 2–3, the illumination system 20 may include a generally circular array 30 of upward-pointing LED's 32 mounted at a bottom portion of a housing 34 of the illuminator 20. A generally circular array of cylinders 36 centered about a central axis Z of illuminator 20 is mounted above the array of LED's 30, with the axis of each cylinder 38 being coincident with the optical axis of a corresponding LED 32 in array 30. The bottom surface 40 of each cylinder 38 is mirrored and angled to a predetermined degree $\theta$. In the embodiment shown, the surface 40 is angled at 22.5 degrees from horizontal. Alternatively, mirrors may be positioned within the cylinders 38 so as to be selectively adjustable, allowing the angle $\theta$ of the reflecting surface to be adjusted if desired. The mirrors 40 reflect the LED light down onto the containers 14 at a predetermined angle $\phi$, which in the embodiment shown is approximately 45 degrees from horizontal. The LED array 30 is strobed briefly (to freeze motion) each time a container 14 is directly underneath the illuminator 20.

Each mirrored cylinder 38 has an axial shaft 42 carrying a spur gear 44, as best shown in FIG. 3. Every other one of these spur gears 44, referred to collectively as set "A", mate with a large annular drive gear 50, forming a planetary gear system. The remaining spur gears 44, referred to collectively as set "B", mate with and are driven by one of their neighboring set A spur gears. As the annular drive gear 50 rotates in a particular direction, for example-clockwise, it drives the set-A gears counter-clockwise, and the set-B gears, which are driven by the set-A gears, clockwise. For a given angular displacement $\beta$ of the annular drive gear 50, all set-A gears will rotate a given angle $\alpha$ in one direction, while all set-B gears will rotate the same angle a in the opposite direction.

One of the cylinder axial shafts 52 of the set A gears is made longer than the others, and carries a gear 54 which mates with a worm gear 56. The worm gear 56 is driven by a hand crank 58, so that an operator can drive the entire constellation of gears 44, 50 by turning the crank 58. The worm gear 56 allows for fine adjustment and prevents unwanted motions of the gears 44, 50. Alternatively, the worm gear 56 can be driven by a motor or other suitable mechanism if desired.

During set up of the illuminator 20, all the mirrors or mirrored surfaces 40 are initially adjusted so that all the LED light substantially converges at a single focal point 60 located on the central axis of the illuminator 20 at a distance h below the plane of the mirrors 40, where R is the radius of the LED array 30 as well as the corresponding array of mirrored cylinders 36. The position of each mirrored cylinder 38 may be adjusted by turning each LED 32 on, one-at-a-time, and adjusting the orientation of its corresponding mirrored cylinder 38 by loosening a set screw 62 holding the spur gear 44 to the cylinder shaft 42. Once these adjustments are made and the set screws 62 re-tightened, the gearing maintains precise coordination of the orientations of all the mirrored cylinders 38.

Figure 6:
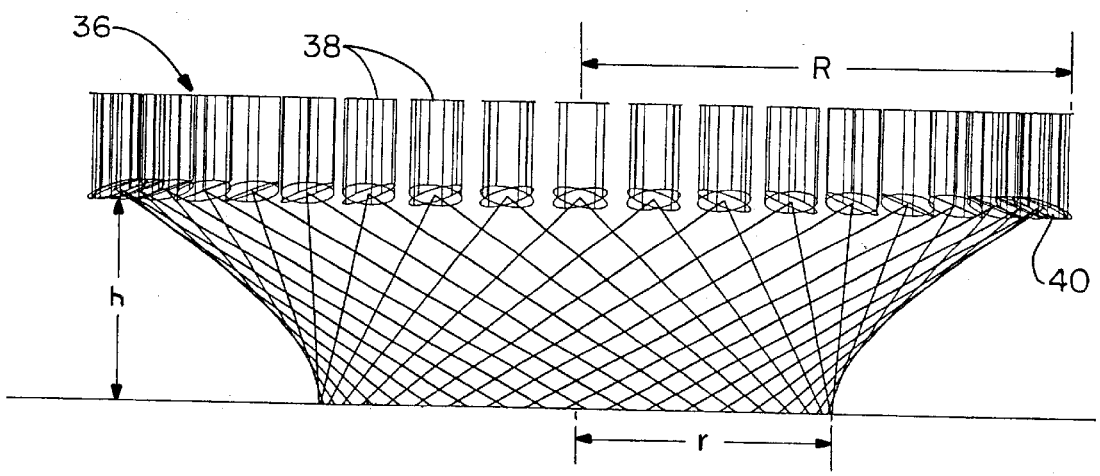
FIG. 6 is a side view of the illumination paths of illumination sources in the array of the illumination system according to the invention.

One feature of the gearing arrangement is that it coordinates the mirrors 40 so the LED light is always substantially focused onto a circle of radius r, as shown in FIG. 6, which is generally parallel to and concentric with the LED array 30, and located a distance h below the plane of the mirrors 40. The quantities r, h and R (the radius of the LED array) satisfy the Pythagorean relation $R^2 = r^2 + h^2$. Another feature of the gearing arrangement is that the oppositely-rotating set-A and set-B mirrors 40 direct light onto the focal circle from opposing or different directions.

Figure 4:
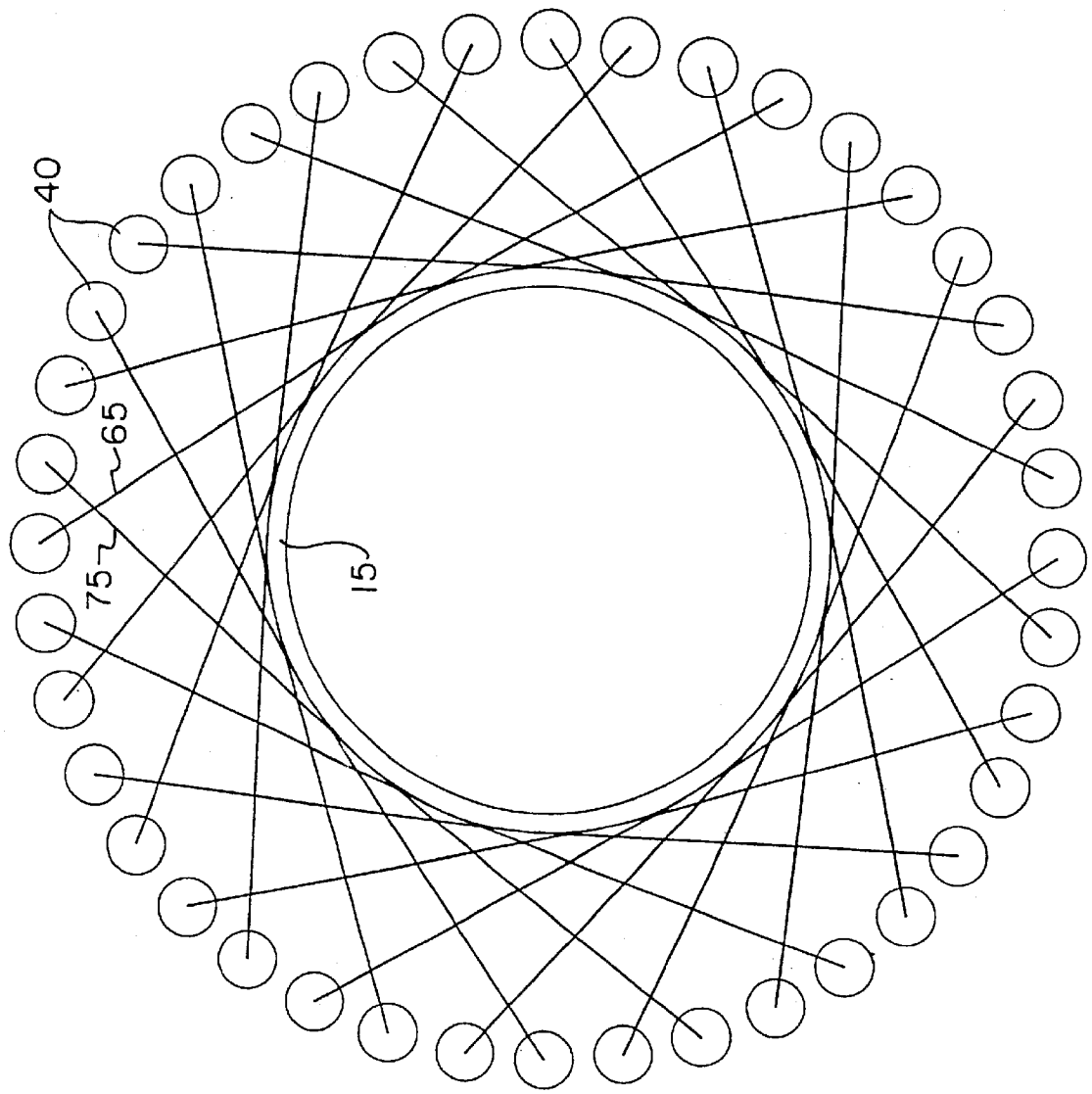
FIG. 4 is a schematic view of the illumination paths of illumination sources in the array of the illumination system according to the invention.
Figure 5:
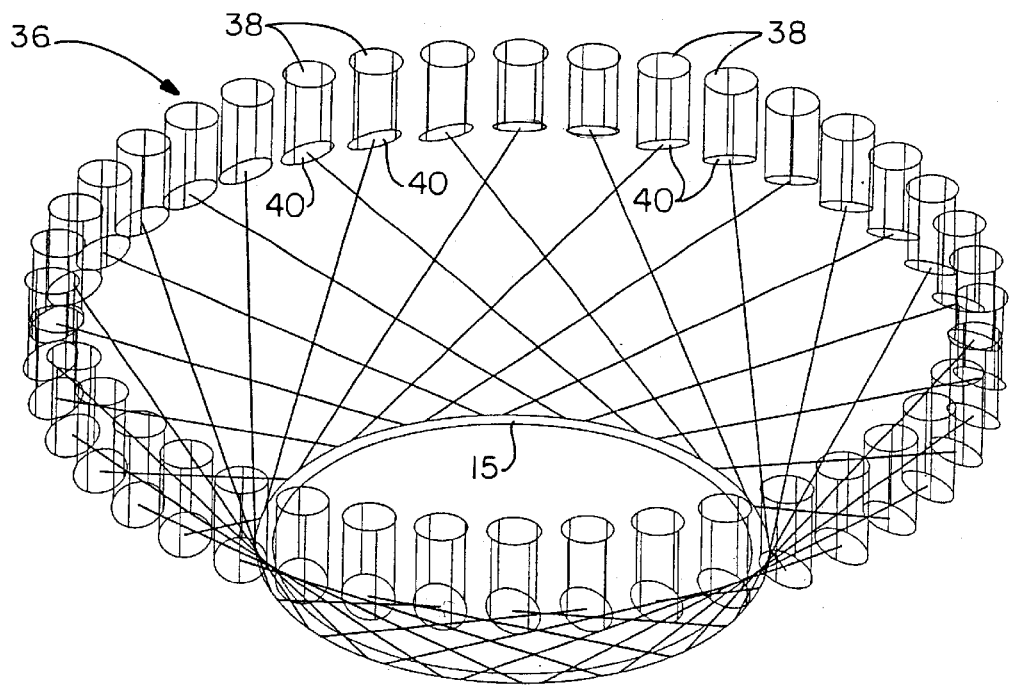
FIG. 5 is a perspective view of the illumination paths of illumination sources in the array of the illumination system according to the invention.

Given an illuminator 20 with an LED array of radius R and a glass container with a sealing surface of radius r located a distance h below the plane of the mirrors, one can adjust the spur gears 44 so the focal circle coincides with the sealing surface 15. When so adjusted, the desired illumination conditions are provided. In this embodiment, for use in inspecting the sealing surface 15 of a glass container 14, the illumination system 20 is designed to direct illuminating radiation only on a predetermined portion of the container 14, such as the sealing surface 15. If light were incident upon other surfaces of the container or the surrounding environment, spurious reflections could be generated. The analysis of a generated image would then be susceptible to misinterpretation or defects misidentified, and non-defective containers 14 may inappropriately be discarded. The illumination system 20 also provides dark field illumination in this embodiment, as the illuminating radiation is directed at the sealing surface 15 at an angle which will not reflect light back to the camera 16. Thus, only defects in the sealing surface 15 will produce reflections that will be monitored by the image acquisition system or camera and processing system 22. The light from the illumination system 20 can be thought of as being directed to a circle which may correspond to the sealing surface 15. An imaginary cylindrical surface containing the circle will be tangential to the light rays from system 20, and all light is made to intersect the circle from above at a predetermined angle φ, such as the 45 degree angle shown. In this manner, no light is reflected from a non-defective sealing surface 15 as desired. The predetermined angle φ can vary from nearly perpendicular to the plane of the circle, so as not to cause direct reflections from a normal surface 15. The system 20 also provides uniform illumination over the entire sealing surface 15, ensuring detection of any defects. Illumination over the entire surface 15 also avoids the need to rotate or otherwise physically manipulate the containers 14 being inspected, allowing for high-speed inspection with accuracy. Each point on the sealing surface 15 also receives incident illuminating light from opposing directions as seen in FIGS. 4–6. Thus, in the embodiment shown, each point on surface 15 has light incident thereon from opposite 45 degree angles, such that defects, such as asymmetric defects, which may otherwise not be adequately detected, will be. Many defects are more easily visualized and identified by light from one or the other direction. As seen in FIGS. 4–6, the locus of light rays forms a helical pattern, with a narrow waist at the sealing surface circle. Both a clockwise helical light pattern 65 and a counter-clockwise helical light pattern 75 are provided. The diameter of the light field produced can be selectively adjusted by means of the gearing arrangement as previously described, allowing different containers to be easily inspected with the same illumination system.

Although the design of the illumination system of this embodiment has been described with reference to specific elements, it should be recognized that other mechanical arrangements to perform the desired functions are contemplated. For example, the coordinated motion of the mirrors could be performed by having each spur gear mate with both of its neighbors, forming a ring of mated gears. Another approach would be to replace the spur gears with pulleys and thread a drive belt around them so that adjacent pulleys rotate in opposite directions. Alternatively, the pulleys and drive belt could be replaced with sprockets and a drive chain. Other functionally equivalent embodiments are also contemplated. Further, light sources other than LED's could be used, such as laser diodes, fiber optics or collimated incandescent bulbs. Also, any illuminating radiation may be used, not just visible light. Additionally, there can be provided focusing or diffusing lenses between the LED's and the mirrors, or between the mirrors and the object. For example, lenses could be provided in association with the LED's to collimate the beams projecting onto the sealing surface.

Although the invention has been described with reference to particular embodiments, various modifications or alterations are contemplated in the scope of the invention. The invention is therefore not to be limited to the embodiments shown and described, and includes all such modifications defined in the appended claims.

What is claimed is:

1. An illumination system for inspecting a predetermined surface of an object comprising:
   a means for projecting a first plurality of collimated light beams at a first angle of incidence onto said predetermined surface and over substantially the entire predetermined surface of said object;
   a means for projecting a second plurality of collimated light beams at a second angle of incidence onto said predetermined surface and over substantially the entire predetermined surface of said object;
   a means for recording an image of said illuminated surface; and
   a means for adjusting said first and second pluralities of collimated light beams to match said predetermined surface of said object to be inspected;
   wherein said means for adjusting said first and second pluralities of collimated light beams comprises a first and second set of gears positioned to simultaneously adjust a diameter formed by said first and second pluralities of collimated light beams.

2. The illumination system of claim 1, wherein said means for recording an image of said surface comprises a camera.

3. The illumination system of claim 1 further comprising an object positioning sensor which determines when said surface of said object is properly positioned with respect to said means for recording an image of said surface.

4. The illumination system claim 1 further comprising an image inspection system for evaluating whether said image shows a defect on said surface of said object.

5. The illumination system of claim 1 further comprising an object rejection system which selectively segregates said objects based on whether any defects.

6. An illumination system for inspecting a predetermined surface of an object comprising:
   a means for projecting a first plurality of collimated light beams at a first angle of incidence onto said predetermined surface and over substantially the entire predetermined surface of said object;
   a means for projecting a second plurality of collimated light beams at a second angle of incidence onto said predetermined surface and over substantially the entire predetermined surface of said object, and
   a means for recording an image of said illuminated surface;
   wherein said means for projecting said first plurality of collimated light beams comprises a first set of a plurality of mirrored surfaces positioned above a first plurality of light sources.

7. The illumination system of claim 6 in which said means for projecting said second plurality of collimated light beams comprises a second set of a plurality of mirrored surfaces positioned above a second plurality of light sources are detected on said surface of said object.

8. The illumination system of claim 7 in which said first set and said second set of said plurality of mirrored surfaces are coaxially positioned, each generally in a circular pattern.

9. The illumination system of claim 7 in which said first set and said second set of said plurality of mirrored surfaces are each formed on a rotatable body.

10. The illumination system claim 9 in which each of said rotatable bodies comprises at least in part a gear engaged with at least one other gear of an adjacent rotatable body of said rotatable bodies.

11. The illumination system claim 9 in which said rotatable bodies of said first set of said plurality of mirrored surfaces rotate in opposite directions from said rotatable bodies of said second set of said plurality of mirrored surfaces.

12. A machine vision system for inspecting a predetermined surface of an object comprising:
- an illuminator comprising a first plurality of mirrored surfaces which redirect collimated light beams at a first angle of incidence onto said predetermined surface and over substantially the entire predetermined surface of said object and a second plurality of mirrored surfaces which redirect collimated light beams at a second angle of incidence onto said predetermined surface and over substantially the entire predetermined surface of said object;
- a camera positioned to record an image of said predetermined surface when said surface is illuminated by said illuminator;
- a positioning sensor which determines when said predetermined surface is properly positioned with respect to said camera and said illuminator;
- an image inspection system for evaluating whether said image shows a defect on said predetermined surface; and
- an object rejection system which selectively segregates said objects based on whether any defects are detected on said predetermined surface.

13. The system of claim 12 in which said first and second plurality of mirrored surfaces are simultaneously adjustable such that said redirected collimated light beams form a diameter which can be enlarged or made smaller to correspond with said predetermined surface.

14. A method for inspecting a surface comprising the following steps:
a) providing an object having a predetermined surface:
b) illuminating said predetermined surface with a first plurality of collimated light beams projected at a first angle of incidence onto said predetermined surface and over substantially the entire predetermined surface of said object and a second plurality of collimated light beams projected at a second angle of incidence onto said predetermined surface an over substantially the entire predetermined surface of said object;
c) adjusting said first and second pluralities of collimated light beams to match the diameter of said predetermined surface of said object by simultaneously rotating a first set of a plurality of mirrored surfaces and a second set of a plurality of mirrored surfaces in opposite directions
d) recording an image of said illuminated predetermined surface; and
e) determining whether a defect exists on said predetermined surface.

15. The method of claim 14 further comprising the step of transporting said object toward an illuminator device.

16. The method of claim 14 further comprising the step of determining when said object is in a predetermined position with relation to said illuminator device.

17. The method of claim 14 further comprising the step of segregating said objects having a defective predetermined surface from said objects having an acceptable predetermined surface.

18. A method for inspecting a predetermined surface comprising the following steps:
a) providing an object having a predetermined surface;
b) transporting said object toward an illuminator device;
c) determining when said object is in a predetermined position with relation to said illuminator device:
d) illuminating substantially the entire predetermined surface with both a first and a second plurality of collimated light beams from said illuminator device;
e) adjusting said first and second pluralities of collimated light beams to match the diameter of said predetermined surface of said object by simultaneously rotating a first set of a plurality of mirrored surfaces and a second set of a plurality of mirrored surfaces in opposite directions;
f) recording an image of said illuminated surface;
g) determining whether a defect exists on said predetermined surface; and
h) segregating said object having a defective predetermined surface from said objects having an acceptable predetermined surface.

* * * * *

UNITED STATES PATENT AND TRADEMARK OFFICE
CERTIFICATE OF CORRECTION

PATENT NO.    : 6,621,569 B2
DATED         : September 16, 2003
INVENTOR(S)   : Richard A. Sones It is certified that error appears in the above-identified patent and that said Letters Patent is hereby corrected as shown below:

Column 6,
Line 34, replace "The illumination system claim 1" with -- The illumination system of claim 1 --.
Line 39, replace "any defects." with -- any defects are detected on said surface of said object. --.
Line 60, replace "light sources are detected on said surface of said object." with -- light sources. --.

Column 7,
Line 1, replace "The illumination system claim 9" with -- The illumination system of claim 9 --.
Line 5, replace "The illumination system claim 9" with -- The illumination system of claim 9 --.

Column 8,
Line 2, replace "predetermined surface an over substanially" with -- predetermined surface and over substantially --.

Signed and Sealed this

Tenth Day of February, 2004

JON W. DUDAS
*Acting Director of the United States Patent and Trademark Office*